(12) United States Patent
Kamada et al.

(10) Patent No.: US 6,496,725 B2
(45) Date of Patent: Dec. 17, 2002

(54) APPARATUS FOR DETERMINING DEGREE OF RESTORATION OF DISEASED PART

(75) Inventors: Mitsugu Kamada, Omagari (JP); Yoshinori Fukuda, Akita (JP)

(73) Assignee: Tanita Corporation, Tokyo (JP)

(*) Notice: Subject to any disclaimer, the term of this patent is extended or adjusted under 35 U.S.C. 154(b) by 82 days.

(21) Appl. No.: 09/749,511

(22) Filed: Dec. 28, 2000

(65) Prior Publication Data

US 2001/0007924 A1 Jul. 12, 2001

(30) Foreign Application Priority Data

Dec. 28, 1999 (JP) .......................................... 11-372231

(51) Int. Cl.⁷ ................................................ A61B 5/04
(52) U.S. Cl. ...................................................... 600/547
(58) Field of Search ................................ 600/547, 300, 600/372, 393, 399, 548

(56) References Cited

U.S. PATENT DOCUMENTS

| 4,383,533 | A | * | 5/1983 | Lovelace et al. ........... 600/437 |
| 5,335,667 | A | * | 8/1994 | Cha et al. .................. 600/547 |
| 5,735,284 | A | | 4/1998 | Tsoglin et al. |
| 5,807,272 | A | * | 9/1998 | Kun et al. ................... 600/547 |
| 6,125,297 | A | * | 9/2000 | Siconolfi ..................... 600/484 |
| 6,134,480 | A | * | 10/2000 | Minogue ..................... 600/391 |
| 6,151,523 | A | * | 11/2000 | Rosell Ferrer et al. ...... 600/506 |
| 6,363,722 | B1 | * | 1/2002 | Heethaar et al. ............ 600/547 |

FOREIGN PATENT DOCUMENTS

| WO | WO98/26714 A | 6/1998 |
| WO | WO99/653390 A | 12/1999 |

* cited by examiner

*Primary Examiner*—Gene Mancene
*Assistant Examiner*—Arnold Castro
(74) *Attorney, Agent, or Firm*—McDermott, Will & Emery

(57) ABSTRACT

Disclosed is an apparatus for determining a degree of restoration of a diseased part, comprising: two pairs of electrodes; an electric current source; a voltage measuring unit; and an arithmetic unit. According to the present invention said two pairs of electrodes are contacted with a skin in the surrounding area of the diseased part, and said electric current source feeds a measuring current via selected ones of said electrodes. Furthermore said voltage measuring unit measures a voltage between another selected ones of said electrodes, and said arithmetic unit calculates a parameter representing a degree of restoration of the diseased part based on the measurement data from said voltage measuring unit.

6 Claims, 7 Drawing Sheets

| PARAMETER INPUT |
|---|
| ID : 009876 |
| SEX : MALE |
| AGE : |
| HEIGHT : cm |
| WEIGHT : kg |

APPARATUS FOR DETERMINING DEGREE OF RESTORATION OF DISEASED PART

BACKGROUND OF THE INVENTION

1. Field of the Invention

The present invention relates to an apparatus for determining a degree of restoration of a diseased part on a human body.

2. Description of the Prior Art

There is a symptom known as a lymphatic edema frequently seen after the surgical operation for breast cancer, uterine cancer and other cancer. This is a kind of swell mainly appeared only at one side or on a portion of an arm, a leg or an armpit, that frequently involves no change of color or no pain. That is to say, this is under such condition that a portion is swelled somehow. In an initial stage for the lymphatic edema there is no significant obstacle occurred in the life of a person if he does not concern about it. In addition a physician may not positively deal with such swelled portion and frequently leave it without any treatment. With the progress of such symptom, however, it may happen that the swelled portion becomes larger or suddenly turns red color with a fever, for which the person feels uneasy.

In the past a several types of diagnosis and assessment method for the lymphatic edema have been developed. For instance, a palpation by a physician has been conducted by touching the diseased part with his hand, or a change in circumferential length or volume of the target part has been measured. Alternatively some device with an echo effect has been used to produce an image with which the diagnosis for the diseased part is carried out.

On the other hand, the muscle of a human body consists of an aggregation of fine cells known as muscular fibers. The number of such muscular fibers on a person is naturally determined when he was born and does not increase or decrease thereafter, but each of them may become thicker or thinner. Such phenomenon may be generally expressed by the words "growth or decline of the muscles". If a person had an accident such as fracture of a bone or breakage of a tendon then the diseased part and its surrounding area are covered with a gypsum after the surgical operation in order to protect that part against any movement. Of course, the person should restrain himself from carrying out a physical exercise. Due to the restriction in movement of the person in his daily life the muscle of the person, and in particular, the skeletal muscle becomes declined only in a part such as one arm or one leg. Therefore some rehabilitation is necessary for the person to rapidly restore the declined muscular fibers after removing the gypsum.

In such circumstances the prior art method of knowing a degree of such restoration is simply to measure the muscle power for that part of the person.

The prior art diagnosis and assessment method for the lymphatic edema mainly depend on the subjective decision by the physician, and therefore, there may frequently be some difference in decision and assessment made by the different physicians. In addition, touching the diseased part of the patient with the hand of the physician may cause any possibility of occurrence of pain even some time interval after the surgical operation, which leads to uneasiness for the patient. Then the prior art method is not preferable for the diagnosis for the diseased part that is in the course of restoration.

The prior art method for measuring the muscle power to know the degree of restoration of an external damaged part after the surgical operation is difficult to embody because various types of the measuring devices are necessary and a patient is required to move by himself a part of his body including the diseased part.

SUMMARY OF THE INVENTION

In view of the above it is an object of the present invention is to provide a new and improved apparatus for determining a degree of restoration of a diseased part on a person, that can solve the prior art problems as described above.

To attain such object the present invention provides an apparatus for determining a degree of restoration of a diseased part, comprising: two pairs of electrodes; an electric current source; a voltage measuring unit; and an arithmetic unit; whereby said two pairs of electrodes are contacted with a skin in the surrounding area of the diseased part, said electric current source feeds a measuring current via selected ones of said electrodes, said voltage measuring unit measures a voltage between another selected ones of said electrodes, and said arithmetic unit calculates a parameter representing a degree of restoration of the diseased part based on the measurement data from said voltage measuring unit.

According to one embodiment of the present invention said electrodes of the two electrode pairs are placed on a line at such interval that the diseased part is positioned therebetween.

According to another embodiment of the present invention said apparatus further comprises a display unit and said display unit indicates the parameter produced by said arithmetic unit.

According to further embodiment of the present invention said apparatus further comprises a storage unit and a comparison unit, said storage unit stores the parameter produced by said arithmetic unit, and said comparison unit compares the parameter representing the current measurement data with the parameter representing the previous measurement data stored in said storage unit or the predetermined reference and outputs the result of comparison, which is then displayed on said display unit.

According to yet further embodiment of the present invention said parameter includes a bioelectrical impedance According to yet further embodiment of the present invention said parameter includes an information on a swell in the surrounding area of the diseased part.

According to yet further embodiment of the present invention said parameter includes an information on an amount of muscle in the surrounding area of the diseased part.

According to yet further embodiment of the present invention said parameter includes a ratio of intra-cellular water to extra-cellular water.

According to yet further embodiment of the present invention said current source selectively feeds the measuring current having any one of a plurality of frequencies.

BRIEF DESCRIPTION OF THE DRAWINGS

Now the present invention will be described in more detail with reference to the accompanying drawings in which.

DESCRIPTION OF THE PREFERRED EMBODIMENTS

Figure 1:
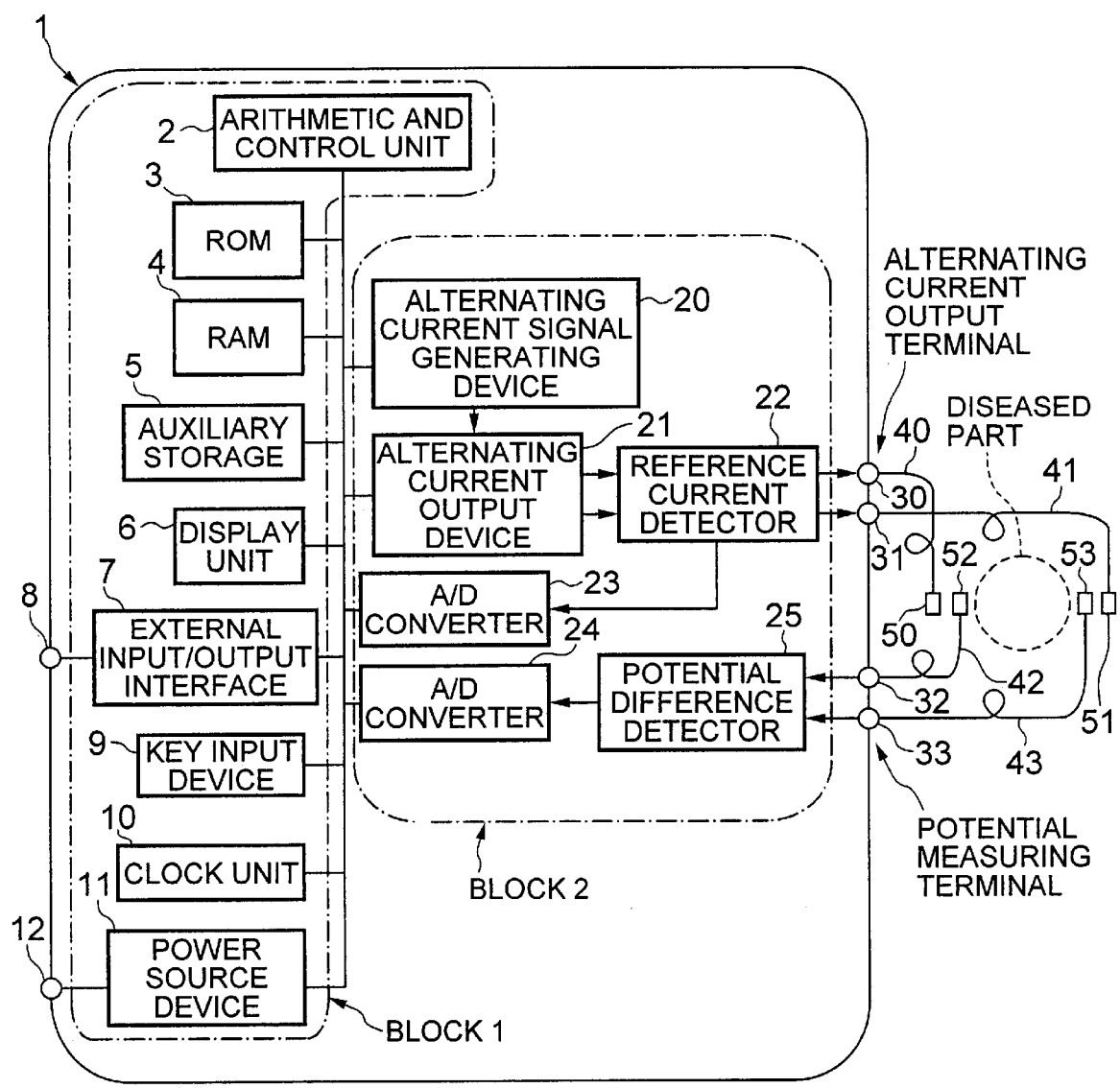
FIG. 1 is a block diagram illustrating an apparatus for determining a degree of restoration of a diseased part according to one embodiment of the present invention.

Referring first to FIG. 1 an apparatus for determining a degree of restoration of a diseased part on a person according to an embodiment of the present invention is entirely shown in the form of a block diagram. As shown in FIG. 1, the apparatus 1 for determining a degree of restoration of the diseased part according to the present invention is generally segmented into two blocks, i.e. a block 1 and a block 2. The block 1 is configured to mainly perform a control for the bioelectrical impedance measurement, an arithmetic operation and an input/output of the data. The block 1 comprises: an arithmetic and control unit 2; a ROM 3 for storing constants and programs for an apparatus control and the arithmetic operation; a RAM 4 for temporarily storing a measured data, an arithmetic result, and data and programs read out from an external device; a nonvolatile auxiliary storage 5 allowing the measured data, the arithmetic result and a parameter regarding the measurement to be stored, read out or updated; a display unit 6 for indicating an information for operation, a condition during measurement, the measured data and the arithmetic result; an external input/output interface 7 for outputting a parameter and measured data to an external device and for reading a parameter regarding the measurement and a control information or a control program for the measurement into the present apparatus from the external device; an external interface terminal 8 for connecting the external input/output interface 7 to the external device; a key input device 9 for inputting a control command for the apparatus and a personal parameter of a person to be measured; a clock device 10 for generating a time information for controlling a date and time of the measurement; a power source device 11 for supplying an electric power to each unit of the present apparatus; and a power source terminal 12 for supplying the electric power to the power source device 11 from the outside.

Figure 11:
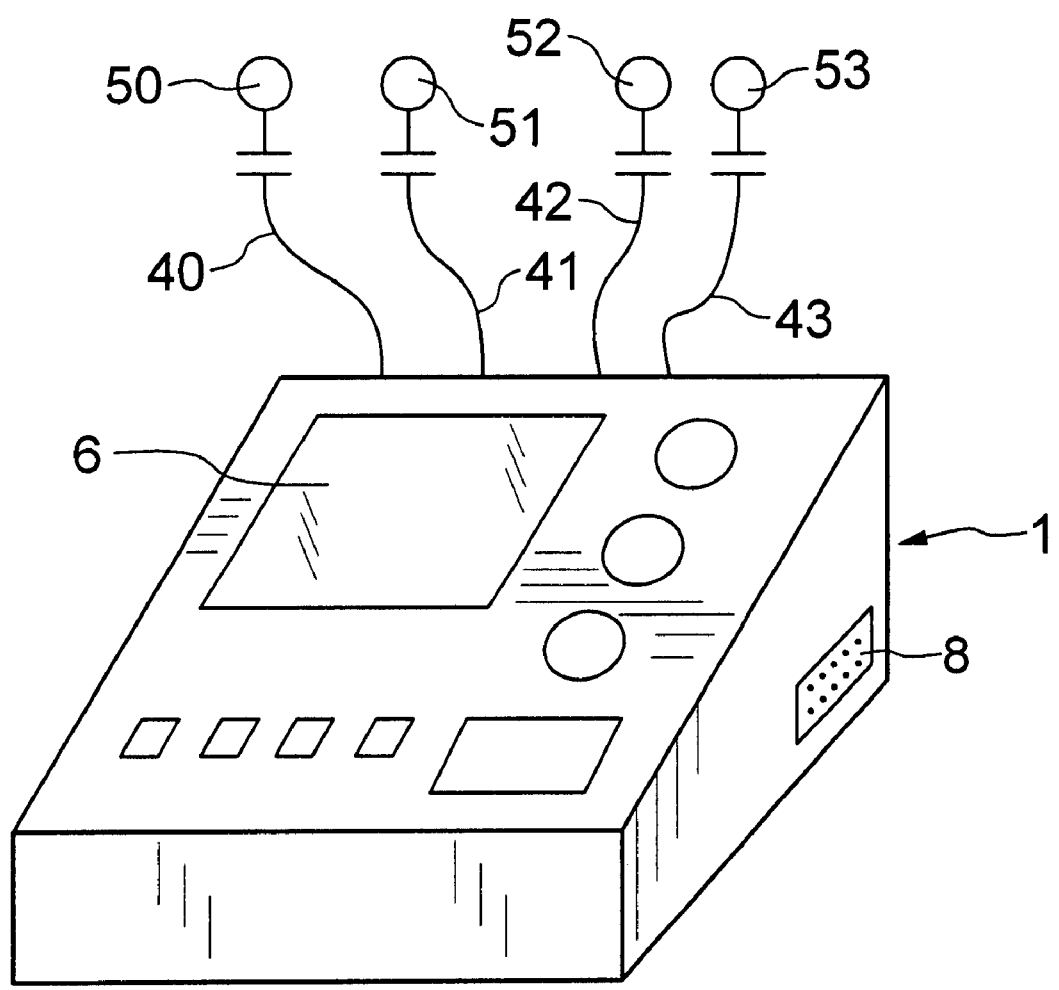
FIG. 11 is an external view illustrating the apparatus for determining a degree of restoration of a diseased part according to the present invention.

The block 2 is configured mainly to measure the bioelectrical impedance and to convert an analog signal thereof into a digital signal. The block 2 comprises an alternating signal generating device 20 for generating an alternating current signal with a frequency defined by a control program stored in the ROM 3 or the RAM 4; an alternating current output device 21 for applying to an object to be measured the alternating signal output from the alternating signal generating device 20 with an RMS value defined by the control program stored in the ROM 3 or the RAM 4; a reference current detector 22 for detecting a current applied to the object to be measured and for outputting it as a reference current detection signal; alternating current output terminals 30 and 31 which are output terminals for applying to the object to be measured an alternating current supplied from the alternating current output device 21 through the reference current detector 22; an A/D converter 23 for converting an analog signal, which is an output of the reference current detector 22, to a digital signal; potential measuring terminals 32 and 33 which are input terminals for inputting potential signals from the object to be measured at two points thereof respectively; a potential difference detector 25 for outputting a differential signal of the potential signals between the potential measuring terminals 32 and 33; and an A/D converter 24 for converting an analog signal, which is an output of the potential difference detector 25, to a digital signal. FIG. 11 is an external view illustrating the entire apparatus 1 configured to include all the components and devices as described above.

Next, description will be made to how to attach the electrodes when it is desired to determine a degree of restoration of the diseased part that may cause a lymphatic edema and the like by using the apparatus 1. The electrodes 50, 51, 52, 53 are placed on a line so that the diseased part to be measured is positioned therebetween, as shown in FIG. 1. More particularly the electrodes are placed in the order of 50, 52, 53, 51 from the outer side, and the diseased part is present between the electrodes 52 and 53. The electrodes 52 and 53 are spaced from the diseased part at the predetermined distance, respectively. Similarly the electrodes 50 and 52 as well as 53 and 51 are spaced apart from each other. The alternating current output terminals 30, 31 of the apparatus 1 are connected to the electrodes 50, 51 via cables 40, 41, respectively. Similarly the potential measuring terminals 32, 33 are connected to the electrodes 52, 53 via cables 42, 43, respectively. The corresponding pairs of the terminals and the electrodes are: 30–50; 31–51; 32–52; and 33–53.

Figure 2:
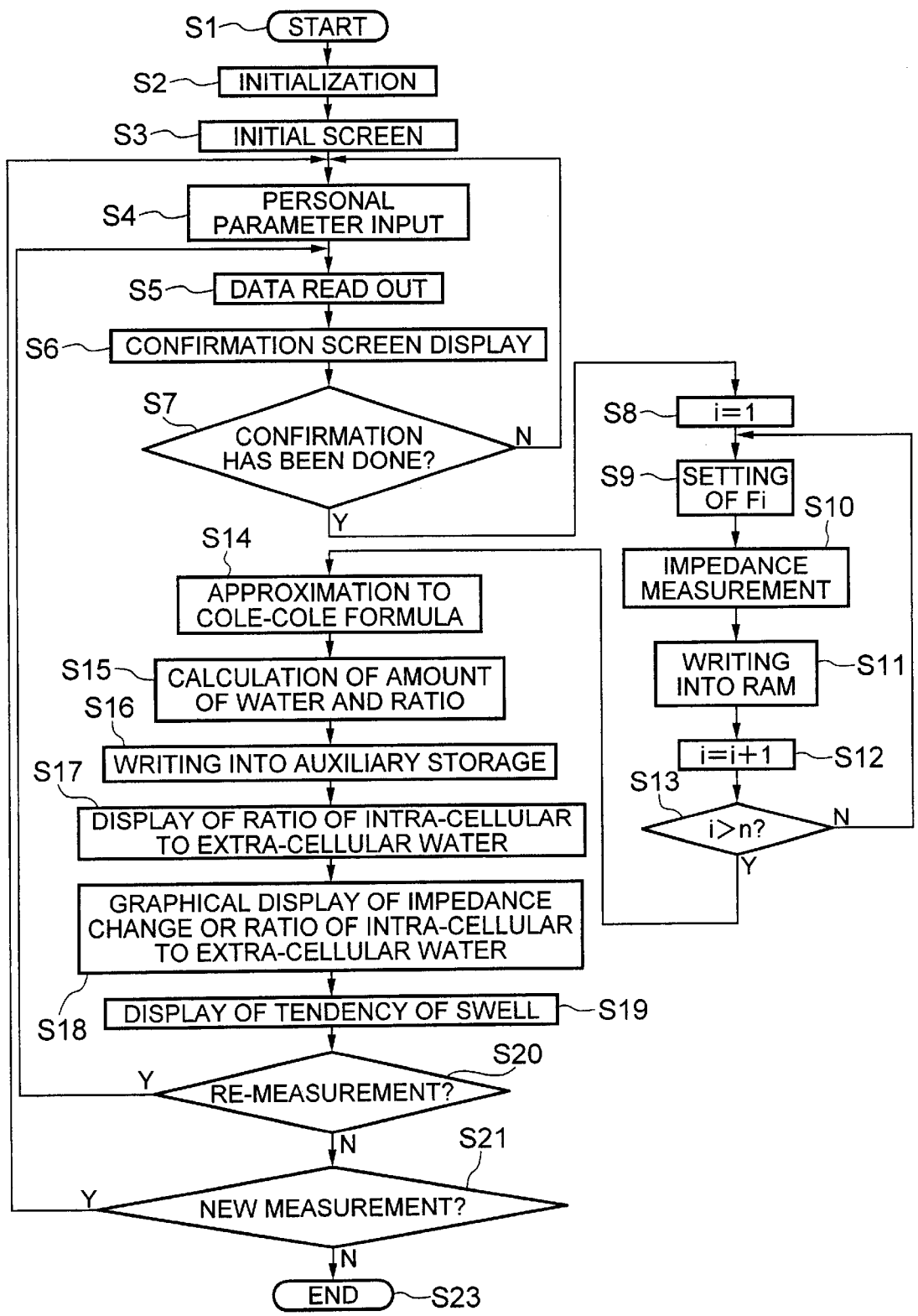
FIG. 2 is a flow chart illustrating a measurement procedure using a plurality of frequencies conducted by the apparatus in FIG. 1.

Then a measurement and decision procedure and an operation of the present embodiment will be generally described with reference to the flow chart shown in FIG. 2.

Figures 3, 4:
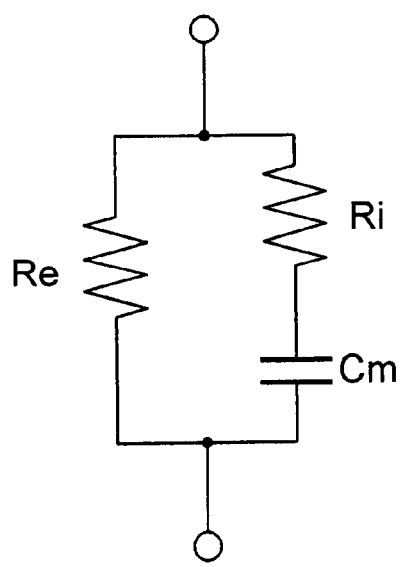
FIG. 3 is a view illustrating a personal parameter entering screen in the embodiment in FIG. 1.
FIG. 4 is an electrically equivalent circuit of a cell in a tissue.

When a power switch of the apparatus being turned ON at step S1, the apparatus is initialized (step S2) and simultaneously an initial screen is indicated on the display unit 6 for a few second (step S3). Then, a screen for inputting a personal parameter shown in FIG. 3 is indicated on the display unit 6 to enter a wait mode. Then an identification number of a person to be measured and the personal parameters thereof including a sex, a height, a body weight and an age are input through the key input device 9. In this connection it is preferred that such personal parameters are input in advance and they are read out and used every time when the identification number of the person is entered. The present embodiment is configured, however, such that the measuring can be performed even if these parameters are not set. When the personal parameters are not set, however, an arithmetic operation for calculating a body composition is not executed as described later.

When the identification number is input (step S4), the personal parameters stored in RAM 4 is read out (step S5) and a screen for confirming that the personal parameters stored and read out are correct is displayed on the display unit 6 (step S6). If they are correct the procedure proceeds to a routine for measuring a bioelectrical impedance, but if not, the procedure returns to the step 4 for inputting the identification number (step S7).

A measuring operation of the bioelectrical impedance starts when a measuring start key is pushed whether or not the personal parameters have been set. It is a matter of course that the electrode for the measurement should have been attached to the person to be measured and should have been connected to the apparatus before starting the measurement.

Then the description will be made to the measurement of the bioelectrical impedance based on which the degree of restoration of the diseased part is determined.

The measurement of the bioelectrical impedance is repeated "n" times ("n" is already set), beginning with the frequency F1 of the frequency Fi.

In step S8 the initial setting for the first frequency is performed so that "i"=1, and in step S9, this value of "i" is used to set the frequency Fi.

An output signal frequency is set by the alternating signal generating device 20 based on a measurement control parameter stored in advance in the ROM 3 or on the measurement control parameter set in the RAM 4 through the auxiliary storage 5 or the external input/output interface 7. An output signal from the alternating signal generating device 20 is input to the alternating current output device 21. The alternating current output device 21 is composed of a constant current output circuit whose current value can be optionally set. The output current value of the alternating current output device 21 is set based on the measurement control parameter. The alternating current output from the device 21 is applied to the person to be measured through the reference current detector 22, the alternating current output terminals 30 and 31, the measurement cables 40 and 41 connected to respective terminals, and the electrodes 50 and 51 for applying a measuring current.

At that time, the current applied to the person to be measured is detected by the reference current detector 22. The detected output in the form of analog signal is converted to the digital signal by the A/D converter 23, and the resulting signal is stored in the RAM 4. Simultaneously, potential signals are picked up by the potential measuring electrodes 52 and 53 attached to the person to be measured. Then the signals are fed via the measuring cables 42 and 43 connected to respective electrodes, and the potential measuring terminals 32 and 33 connected to respective measuring cables, to the potential difference detector 25. The potential difference detector 25 in turn outputs the potential difference signal, which corresponds to the difference between the potential signals input thereto, into the A/D converter 24. The A/D converter 24 converts the input potential difference signal in the analogue format into the digital signal, which means that the bioelectrical impedance is measured (step S10). Then the resulting signal is stored in the RAM 4 (step S11).

When the measurement of the bioelectrical impedance at the first frequency is completed the setting of i=i+1 is performed (step S12) and decision is made as to whether the predetermined number of times "n" is over or not (step S13). If "i" is greater than the predetermined number "n" the measurement of the bioelectrical impedance is terminated.

But if not, the procedure returns to step S9 and the measurement of the bioelectrical impedance is repeated, but at the second frequency.

Then the vector impedance locus and the parameters associated thereto are calculated based on the measured values at each of plural frequencies.

A bioelectrical impedance of a living body is typically represented by a lumped constant equivalent circuit comprising an extra-cellular fluid resistance Re, an intra-cellular fluid resistance $R_i$, and a cell membrane capacitance Cm, as shown in FIG. 4. Practically, plural cells making up the living body are respectively represented by individual circuits having different constants due to their different shapes and characteristics. Thus, in the living body as an aggregation of such cells, its vector impedance locus does not show a semicircle at variance with the case of measuring the lumped constant equivalent circuit, but shows a circular arc given in the Cole-Cole model.

Figure 5:
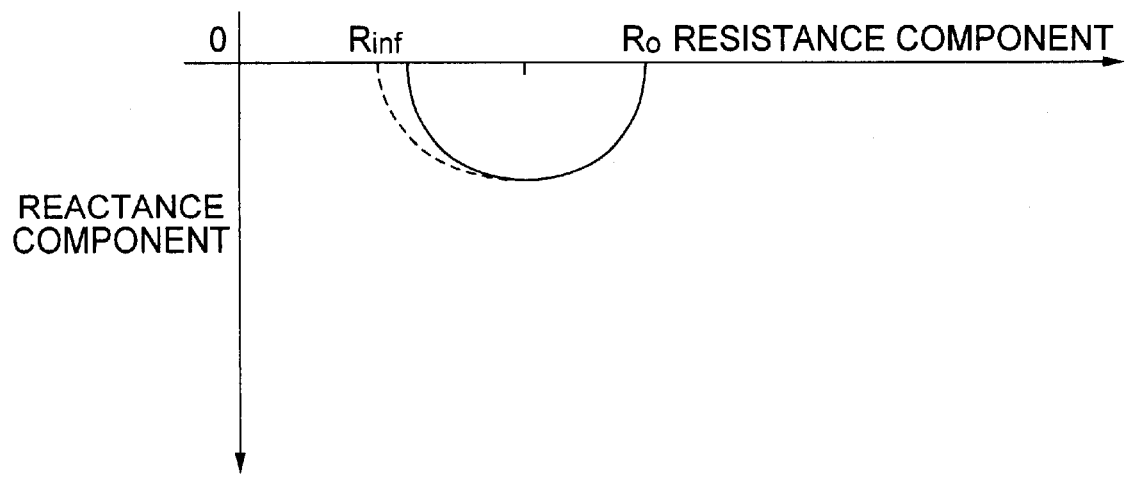
FIG. 5 is a graphical representation of a bioelectrical vector impedance locus of a human body.
Figure 6:
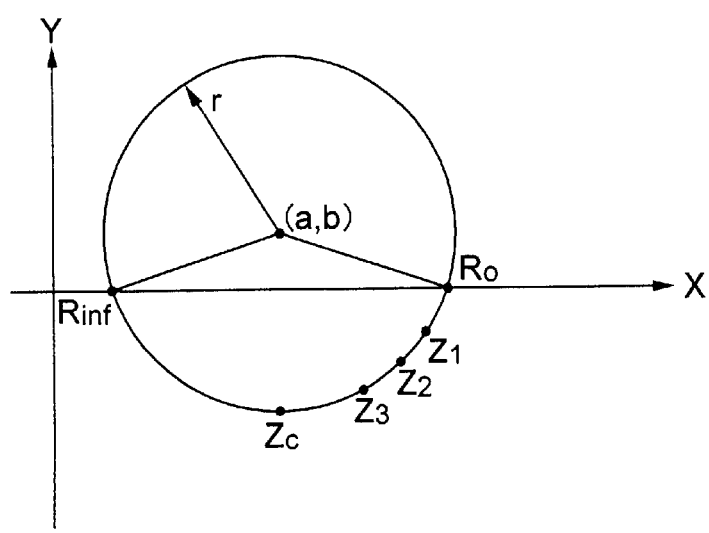
FIG. 6 is a graphical representation illustrating a relation between a point of characteristic frequency and points of 0 Hz and infinite frequencies.

Thus, the bioelectrical impedance of the living body is generally represented by a circular arc-like locus shown in FIG. 5. In FIG. 5, x-axis represents a resistance component of the impedance, while y-axis represents a reactance component of the impedance. Since the reactance component of the bioelectrical impedance shows a negative value due to its capacitive property, the vector locus of the bioelectrical impedance is plotted on the underside of the real axis as shown in FIG. 6. Assuming that the vector impedance locus derived is a circular arc, the bioelectrical impedance values Z1, Z2 . . . Zn measured respectively at the frequencies Fi (i=1–n) are on a circular arc of a certain circle as shown in FIG. 6. Herein, a real axis (axis of abscissa) and an imaginary axis (axis of ordinate) in the vector impedance plane are described as an X-axis and a Y-axis respectively.

Then, one correlation function as expressed below is derived from the impedance Zi (i=1–n) plotted on the coordinate:

$$(X-a)^2+(Y-b)^2=r^2 \tag{1}$$

where, "a" is X coordinate of the center of the circle, "b" is Y coordinate of the center of the circle, and "r" is a radius of the circle.

In other words, this is an approximated correlation expression between points "n". Then the following formula is derived:

$$X=a\pm\sqrt{(r^2-b^2)}$$

wherein, since $R_0 > R_{inf}$, $$R_0=a+\sqrt{(r^2-b^2)}$$
$$R_{inf}=a-\sqrt{(r^2-b^2)}$$

Accordingly, Re and Ri of the equivalent circuit of FIG. 4 are expressed as:

$$Re=R_0$$

$$Ri=R_0 \cdot R_{inf}/(R_0-R_{inf})$$

Since the impedance vector Zc at the characteristic frequency Fc is defined by a point where the reactance or the imaginary axis component, that is, the absolute value of Y-axis component, takes a maximum value, X coordinate as a real axis component and Y coordinate as an imaginary axis component of the impedance vector Zc are determined as:

$$X=a, Y=b-r$$

and thereby the impedance vector Zc is represented as:

$$Zc = a + j(b-r)$$

According to Cole-Cole model described above, the impedance vector at a frequency $\omega$ is expressed as:

$$Z(\omega) = R_{inf} + (R_0 - R_{inf})/(1 + (j\omega\tau)^\beta)$$

where, $Z(\omega)$ is the impedance vector at $\omega$, and $\tau$ and $\beta$ are constants.

When $\tau = 1/\omega c$, $$Z(\omega) = R_{inf} + (R_0 - R_{inf})/(1 + (j\omega/\omega c)^\beta)$$

where $\omega c = 2\pi Fc$.

Fc and $\beta$ can be calculated also based on these relations and a data on the circle (step S14).

Then the body composition values including the amount of extra-cellular water, the amount of intra-cellular water, the ratio of the intra-cellular water to the extra-cellular water, the total body water, the fat free mass, body fat mass and the body fat rate are calculated based on the vector impedance locus and the associated parameters, such as $R_0$, $R_{inf}$, $R_e$, Ri, Zc, Fc or the like, which are calculated beforehand (step S15). If the personal parameter has not been set, this process is omitted as described above.

The resultant data is stored in the auxiliary storage 5 (step S16), together with the date and time data fed from the clock unit 10.

Figure 7:
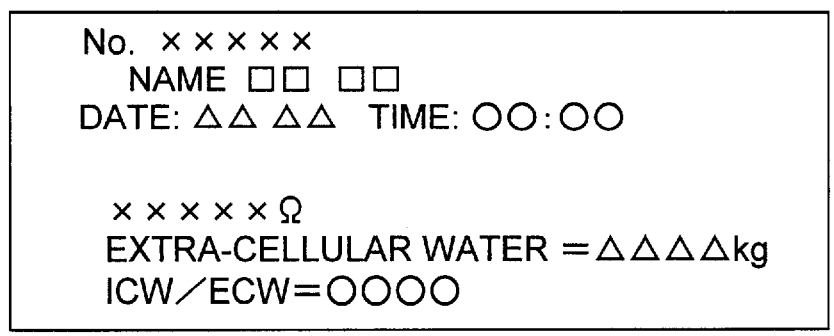
FIG. 7 is a view showing a format in which the measurement result produced in the embodiment in FIG. 1 is indicated.
Figure 8:
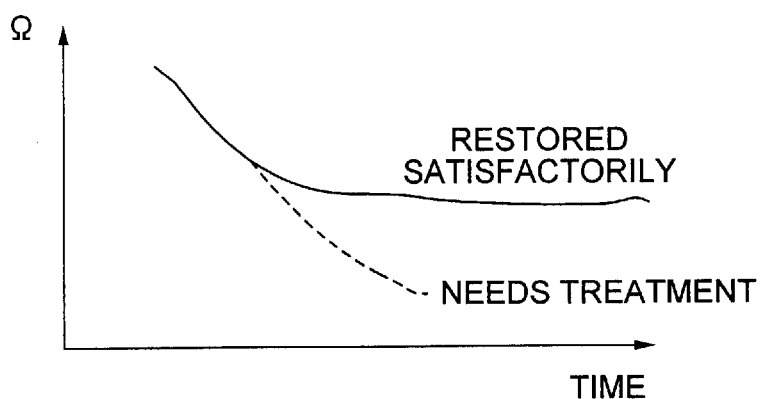
FIG. 8 is a graphical representation showing an impedance change produced in the embodiment in FIG. 1.

The bioelectric impedance, the amount of extra-cellular water, and the ratio of the intra-cellular water to the extra-cellular water (ICW/ECW) already measured and calculated are displayed on the display unit 6 in a format as shown in FIG. 7 (step S17). Then the previous measurement data and the newly stored measurement data are retrieved from RAM 4. If the personal parameter has not initially been set, only the impedance change is displayed on the display unit 8, as shown in FIG. 8.

Figure 9:
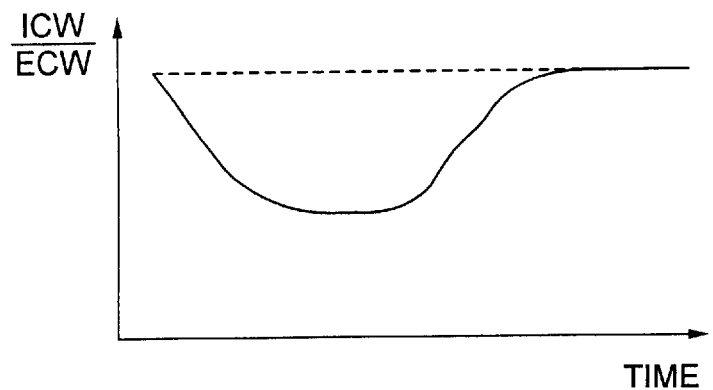
FIG. 9 is a graphical representation showing a change in amount of extra-cellular water and a change in ratio of intra-cellular water to extra-cellular water produced in the embodiment in FIG. 1.

On the other hand, if the personal parameter has been set, the ratio of the intra-cellular water to the extra-cellular water (ICW/ECW) is calculated also in association with the current measurement data. The change in amount of extra-cellular water and the change in ratio of the intra-cellular water to the extra-cellular water are displayed on the display unit 6 in a graph form, as shown in FIG. 9 (step S18). If a significant increase can be seen in the graph showing the change in amount of extra-cellular water, as compared to the previously stored measurement data, the tendency of "being swelled" is indicated on the display unit 6. In contrast thereto, if less change in amount of extra-cellular water can be seen in the graph, the "satisfactory" condition is indicated on the display unit 6 (step S19).

The lymphatic edema frequently seen after the surgical operation for breast cancer and uterine cancer is defined as a swelled condition caused due to the storage of much protein and water in the subcutaneous tissue around the diseased part. The degree of the lymphatic edema can be determined based on the amount of body water around the diseased part. The change in body water of the human body mainly depends on the change in amount of extra-cellular water. As the result the degree of the lymphatic edema can be determined by measuring the bioelectrical impedance through the diseased part of the human body. Then reference is made to the graph in FIG. 8. This graph shows the change in bioelectrical impedance with the progress of time that is measured through the diseased part after the surgical operation for breast cancer, uterine cancer, or the like. This graph shows the case where the bioelectrical impedance measured immediately after the surgical operation was higher, but it greatly decreased every time when the measurement was done, and after a certain period of time, the bioelectrical impedance became not so greatly decreased. This means that the lymphatic edema caused some period of time after the surgical operation and the degree thereof gradually increased, but thereafter the lymphatic edema did not further grow and there was a tendency towards restoration.

Therefore, the degree of restoration of the diseased part can be determined by observation of the change in bioelectrical impedance, amount of extra-cellular water and ratio of intra-cellular water to extra-cellular water as measured by the present apparatus. This may be achieved by, for instance, comparison of the current measured value with the previous measured value or with the predetermined reference.

In step S20, S21 or S23 "re-measurement", "new measurement" or termination of measurement is displayed on the display unit 6. Then the intended operation is selected and the data is entered through the key input device 9.

The re-measurement means that the measurement is performed once again. In this case the measurement is started from the point where the electrodes are attached. The procedure returns to step S5 where the personal parameters stored are read out. The new measurement means that the procedure returns to step S4 where the identification number is entered. This is mainly used for a group examination. If the re-measurement is not performed the procedure is terminated and the entire apparatus is turned OFF (step S23).

Figure 10:
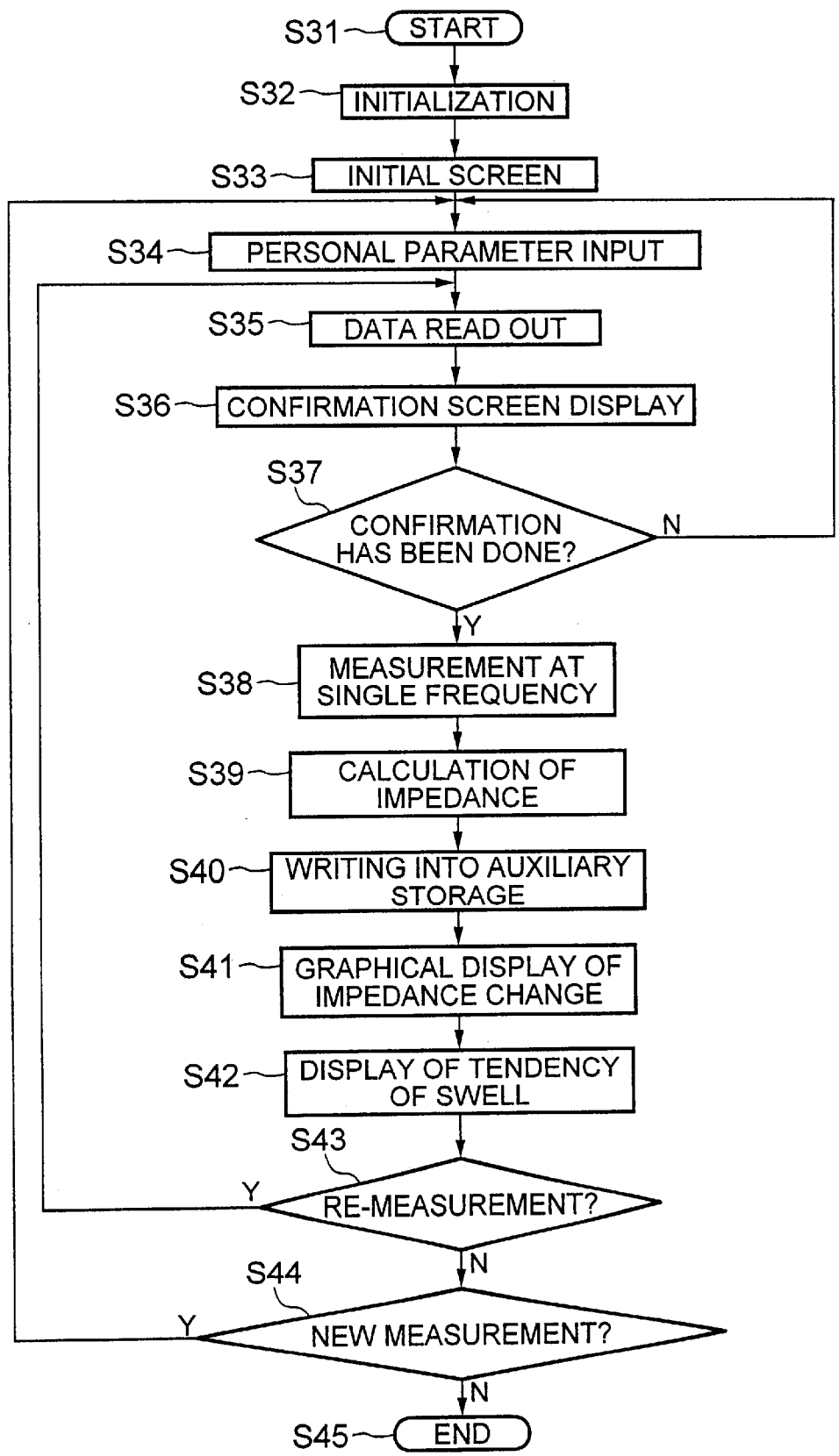
FIG. 10 is a flow chart illustrating a measurement procedure using a single frequency in another embodiment of the present invention.

The embodiment described above is directed to the case where several frequencies are used. The present invention also relates to another embodiment where an alternating current at a single frequency is generated and used in the apparatus for determining the degree of restoration of the diseased part. The block diagram for such second embodiment is same as that in FIG. 1 representing the case of several frequencies used, and therefore, it is omitted here. But, a flow chart representing an operation of the second embodiment where only a single frequency is used is illustrated in FIG. 10.

Then a measuring procedure and an operation of the second embodiment will be described with reference to the flow chart in FIG. 10. An initial operation for the second embodiment is same as the first embodiment where the several frequencies are used. In addition the subsequent operation for the second embodiment where the identification number and the personal parameters are input through the key input device 9 is same as the first embodiment. Therefore the description of steps S31 to S37 is omitted (which steps correspond to steps S1 to S7 as described above). The apparatus according to the second embodiment is started to measure by depressing the measurement start key.

Then the bioelectrical impedance is measured according to the following procedure. Based on the measurement control parameter a single output signal frequency is set by the alternating signal generating device 20. An output signal from the alternating signal generating device 20 is input to the alternating current output device 21.

The alternating current output device 21 sets a single output current value and outputs the corresponding alternating current. This alternating current is applied to a person to be measured through the reference current detector 22 and the alternating current output terminals 30, 31, as in the case of several frequencies used.

At that time, the current applied to the person to be measured is detected by the reference current detector 22. The detected output in the form of analog signal is converted to the digital signal by the A/D converter 23, and the resulting signal is stored in the RAM 4. The potential signals from the potential measuring electrodes 52 and 53 are fed to the potential difference detector 25 and then to the A/D converter 24. The A/D converter 24 converts it into the digital signal, which is stored in the RAM 4. Thus far is the measurement operation (step S38).

Based on the resultant data the bioelectrical impedance is calculated (step S39). Due to the measurement performed at single frequency the impedance calculated is absolute value, rather than vector locus as in the case of the several frequencies used.

Then the amount of body water for the part to be measured is calculated based on this absolute impedance value, provided that the personal parameters have been set.

The resultant data is stored in the auxiliary storage 5(step S40), together with the date and time data from the clock unit 10, as in the case of the several frequencies used.

The resultant data is displayed on the display unit 6. At that time the previous measurement data and the current measurement data are retrieved from RAM 4. Due to the measurement at single frequency the amount of extra-cellular water and the ratio of intra-cellular water to extra-cellular water are not displayed. But the change in bioelectrical impedance is displayed on the display unit 6 in the graph format as shown in FIG. 8, as in the case of several frequencies used (step S41). Any undulation of the curve in the graph indicates whether the swell in the diseased part tends toward "restoration" or needs "treatment" on the display unit 6 (step S42).

Thus far is a series of operation steps for the measurement, and the subsequent step is any one of "re-measurement", "new measurement" and "termination" steps (steps S43 to S45). Such steps are same as the case of several frequencies used.

The apparatus according to the embodiments as described above functions to determine the degree of restoration of the diseased part based on the derived information on the swell such as the lymphatic edema and the like after the surgical operation for breast cancer or uterine cancer. The present invention, however, is not limited to such apparatus, but it is also applicable to determine the degree of restoration of the diseased part based on the derived information on the muscle around the diseased portion after the surgical operation for fracture of a bone.

As already described above the muscle of a human body consists of an aggregation of fine cells known as muscular fibers. If the muscle leaves unused for longer period of time each of the muscular fibers becomes thinner. As the result the blood vessel in the muscle becomes reduced in diameter so that the amount of blood flowing therethrough becomes also reduced. Because of the blood including much electrolyte such as sodium ions or potassium ions it has the characteristic that an electric current is liable to flow therethrough. If the amount of blood decreases the bioelectrical impedance at that part, of course, increases. Therefore the continuous measurement of bioelectrical impedance makes it possible to keep track of the change in amount of the muscle. More particularly when the bioelectrical impedance measured through the surrounding area of the diseased part is higher than the predetermined reference it is determined that the amount of muscle has decreased. On the other hand when the bioelectrical impedance currently measured is lower than that previously measured it is determined that the amount of muscle around the diseased part has satisfactorily been restored under the rehabilitation.

Therefore in order to watch the degree of restoration of the muscle under the rehabilitation after the surgical operation the bioelectrical impedance for the surrounding area of the diseased part is measured by the apparatus configured as shown in FIG. 1 after the surgical operation. Then the bioelectrical impedance is continuously measured at certain interval during the rehabilitation period to keep track of the change in amount of the muscle. Based on the measurement data it is determined that the rehabilitation is satisfactory. The measurement procedure is same as that of the case where the swell is displayed, and therefore, the description thereof is omitted here.

Finally some message such as "the rehabilitation proceeds satisfactorily" or "more physical exercise is necessary" is displayed so that the person to be measured knows the effect of the rehabilitation.

It is apparent from the foregoing that any change in swelled condition can be seen simply by continuously measuring the bioelectrical impedance of the diseased part after the surgical operation for cancer, deriving the amount of body water and displaying the change in bioelectrical impedance in the graph. In addition the need of touching the diseased part is obviated, the better sanitary environment is maintained and the person to be measured feels no pain. This is very useful for a physician to perform diagnosis for a swelled condition of a patient.

The measurement data for a number of persons can be managed by the configuration for connection to the external input/output interface 7.

In case where the apparatus is used in a home a person to be measured can see the tendency of a swell without any assistance of a physician so that the person can easily understand the effect of the rehabilitation by himself.

In addition, after the surgical operation for fracture of a bone, the restoration of the muscle under the rehabilitation against any decline of the muscle through the use of the gypsum can easily be determined simply by continuously measuring the bioelectrical impedance of the diseased part, deriving the amount of body water and displaying the change in bioelectrical impedance in the graph. The rehabilitation that it has been difficult to understand its effect can now encourage the patient because any change in amount of muscle is graphically displayed.

When the bioelectrical impedance is measured using an AC current having plural frequencies and the ratio of intra-cellular water to extra-cellular water is derived on the bases of the impedance vector locus then it is possible to eliminate an error factor of body temperature change after the rehabilitation, which can not be done in case where only the impedance change is observed. This allows more precise determination of the degree of the swelled condition and the restoration for muscle after the surgical operation.

What is claimed is:

1. An apparatus for determining a degree of restoration of a diseased part, comprising:

a plurality of pairs of electrodes;

an electric current source;

a voltage measuring unit;

an arithmetic unit;

a storage unit; and a comparison unit;

wherein said electrodes are for contacting the skin of a user in the area surrounding the diseased part, said electric current source feeds a measuring current via one selected pair of electrodes of said electrode pairs, said voltage measuring unit measures a voltage between another selected pair of electrodes of said electrode pairs, said arithmetic unit calculates an index of swelling in the area surrounding the diseased part representing a degree of restoration of the diseased part based on the measurement data from said voltage measuring unit, said storage unit stores the index of swelling in the area surrounding the diseased part produced by said arithmetic unit as a reference value, and said comparison unit compares the reference value stored in said storage unit with a current index of swelling in the area surrounding the diseased part to determine a degree of restoration of the diseased part.

2. An apparatus for determining a degree of restoration of the diseased part according to claim 1 in which said electrode pairs are placed in a line at intervals such that the diseased part is positioned therebetween.

3. An apparatus for determining a degree of restoration of a diseased part according to claim 1, further comprising a display unit for indicating the degree of restoration of the diseased part based on the index of swelling in the area surrounding the diseased part produced by said arithmetic unit in graphical form.

4. An apparatus for determining a degree of restoration of a diseased part according to any one of claims 1 to 3 in which said index of swelling includes a bioelectrical impedance.

5. An apparatus for determining a degree of restoration of a diseased part according to any one of claims 1 to 3 in which said index of swelling includes an amount of extra-cellular water.

6. An apparatus for determining a degree of restoration of a diseased part according to any one of claims 1 to 3 in which said index of swelling includes a ratio of intra-cellular water to extra-cellular water.

* * * * *